United States Patent [19]

Vaerman

[11] Patent Number: 4,468,620
[45] Date of Patent: Aug. 28, 1984

[54] SYSTEM FOR IN SITU CHECKING OF TURBINE ENGINE BLADES WITH EDDY CURRENT PROBE GUIDANCE APPARATUS

[75] Inventor: Jean F. Vaerman, Vert Saint Denis, France

[73] Assignee: S.N.E.C.M.A., Paris, France

[21] Appl. No.: 312,352

[22] Filed: Oct. 16, 1981

[30] Foreign Application Priority Data

Oct. 16, 1980 [FR] France .................. 80 22100

[51] Int. Cl.³ ...................... G01R 33/00; G01N 27/90
[52] U.S. Cl. .................. 324/261; 73/432 A; 324/262
[58] Field of Search ................. 324/228, 200, 234–243, 324/262, 261, 158 F; 33/1 M; 73/633, 634, 618, 432 A

[56] References Cited

U.S. PATENT DOCUMENTS

| | | | |
|---|---|---|---|
| 2,937,522 | 5/1960 | McGaughey | 73/633 |
| 3,537,300 | 11/1970 | Rapuzzi . | |
| 3,570,304 | 3/1971 | Mihalyak et al. . | |
| 3,588,683 | 6/1971 | Lloyd | 324/241 X |
| 3,739,262 | 6/1973 | Seekins | 324/262 X |
| 4,142,154 | 2/1979 | Couchman . | |
| 4,270,089 | 5/1981 | Haberlein | 324/228 X |
| 4,304,133 | 12/1981 | Feamster | 73/633 |

FOREIGN PATENT DOCUMENTS 2603336 8/1977 Fed. Rep. of Germany .
2051987 4/1971 France .

OTHER PUBLICATIONS

FAA Reliability Symposium Report in Washington, DC, Nov. 18, 1965, pp. 1–9.

Primary Examiner—Gerard R. Strecker
Attorney, Agent, or Firm—Oblon, Fisher, Spivak, McClelland & Maier

[57] ABSTRACT

A system for in situ checking of turbine engine blades consists of a frame bearing on its two opposite large sides two hooks and a stop that can cooperate with the edges of the airfoil portion. Parallel to these sides, the system is provided with two elements serving to guide a carriage which is driven by means of a notched belt and two pinions, of which one is connected to a motor. The carriage supports an elastic element at the end of which is attached a shoe housing the probe. On the side of the shoe is an inclined plane cooperating with an identical inclined plane formed in one of the hooks. The motor is reversible and is controlled by end-of-stroke contacts in the carriage.

8 Claims, 3 Drawing Figures

U.S. Patent  Aug. 28, 1984  4,468,620
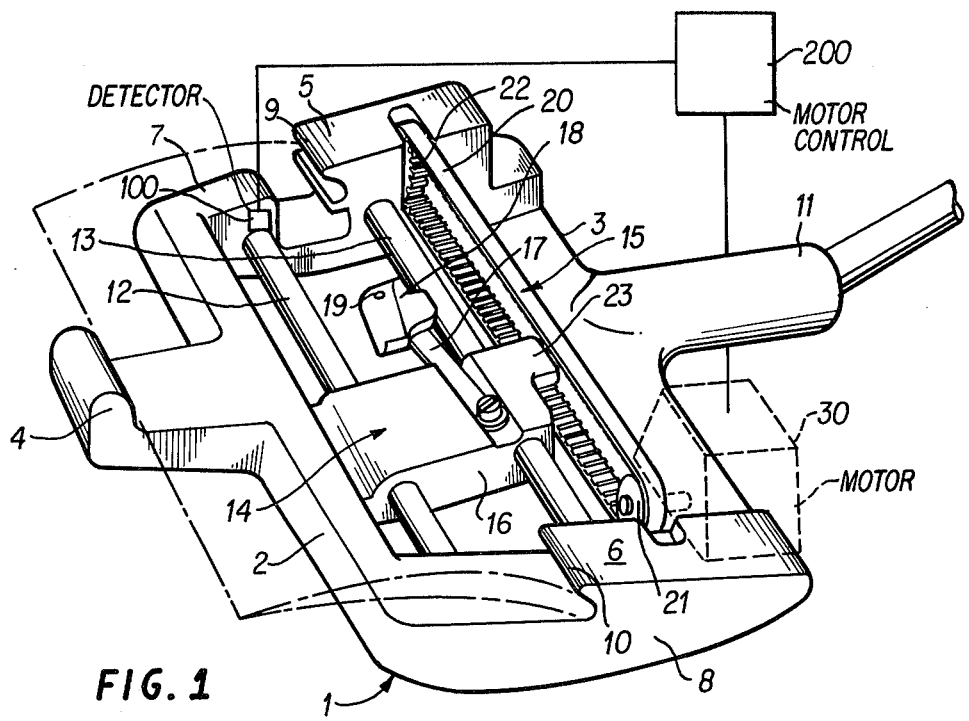
FIG. 1
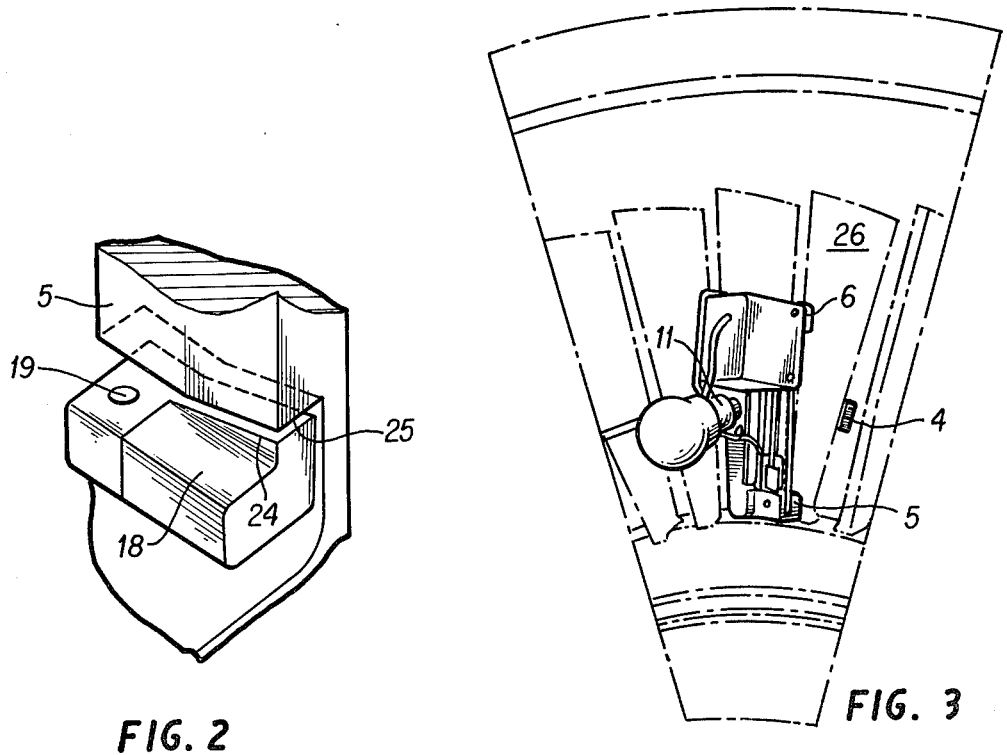
FIG. 2
FIG. 3

SYSTEM FOR IN SITU CHECKING OF TURBINE ENGINE BLADES WITH EDDY CURRENT PROBE GUIDANCE APPARATUS

BACKGROUND OF THE INVENTION

1. Field of the Invention

The invention concerns a system for the in situ checking of turbine engine blades by eddy currents, the system including a unit for positioning the detection probe on the airfoil portion to be checked.

2. Description of the Prior Art

The rupture of a turbine engine blade generally leads to considerable damage. It is therefore important to be able to detect any metallurgical or physical structural defect, not only on the surface but internally. The use of eddy currents, in a known manner, offers this possibility and, with the aid of a probe moved over the surface of the blade, makes it possible to determine the existence and location of the defects.

The position of the probe in relation to the surface explored is an important factor in the precision of the results, and a system making it possible to fix this factor was described at the Federal Aeronautical Agency's symposium on reliability, held in Washington, D.C. on Nov. 18, 1965. That system is composed of a positioning unit, the shape of which matches that of the airfoil portion of the blade, pierced by five ports into which a check probe may successively be positioned. This unit thus perfectly locates the position of the probe in relation to the surface, but has the drawback of not allowing the checking of discrete areas. This point-by-point measurement technique has the drawback of not detecting small defects located between the measurement points.

This problem can be alleviated by equipping the probe with a stop and manually moving the unit in contact with the edge of the airfoil portion. The need for qualified, well-trained personnel in the use of this technique, however, makes it impossible to fully eliminate the difficulties of manual, in situ exploration due to the smallness of the space and, consequently, the reliability of the measurements is not very good.

SUMMARY OF THE INVENTION

The system according to the invention is aimed at limiting as much as possible the manual operations and at obtaining continuous exploration over the entire length of the airfoil portion of the blade that is perfectly reproducible.

According to the invention, the system for in situ checking of turbine engine blades by eddy currents, including a detection probe and a positioning unit, includes a positioning unit consisting of a frame, having on at least two of its sides positioning elements provided to cooperate with at least one of the edges of the blade, as well as elements for guiding the probe and means for rectilinear movement of the probe parallel to an edge of the blade placed in the positioning elements.

BRIEF DESCRIPTION OF THE DRAWINGS

Various other objects, features and attendant advantages of the present invention will be more fully appreciated as the same becomes better understood from the following detailed description when considered in connection with the accompanying drawings in which like reference characters designate like or corresponding parts throughout the several views, and wherein:

FIG. 1 shows a perspective view of the system according to the invention;

FIG. 2 is a partial view of a hook showing the shoe at the end of a stroke; and

FIG. 3 shows the system placed on a blade's airfoil to be checked.

DETAILED DESCRIPTION OF THE PREFERRED EMBODIMENTS

Checking a metallic part for defects requires, as is known, a probe consisting of one or two windings of conductor wire connected to an electronic component making it possible to detect field variations in the coil. The electronic component for detection of defects by eddy currents is well known and will not be described below.

FIG. 1 shows the system according to the invention, consisting of a positioning unit and a probe, the placement of which will be clarified below.

The positioning unit is composed of a frame 1 having two opposite and parallel large sides 2 and 3. Positioning abutments 4, 5 and 6 that cooperate with the trailing and leading edges of the airfoil portion are formed on or parallel to the sides 2 and 3 of the frame.

According to the example shown, two of the abutments 5 and 6 are formed in the small sides 7 and 8 of the frame so that their common axis is parallel to the large sides 2 and 3. The abutments 5 and 6 are in the form of a C-shaped hook and the abutment 4 is in the form of a stop. The distance separating the base of the hooks 5 and 6 from the base of the stop 4 is approximately equal to the width of the blade represented in broken lines. The curved ends 9 and 10 of the hooks 5 and 6 rest on the upper surface of the airfoil portion.

On the side 3, opposite the side 2 bearing the stop 4, the frame is provided with a handle 11 allowing manipulation of the system and its placement on the airfoil portions of the blades of a bladed wheel, as shown in FIG. 3.

Means for guiding the probe are formed by at least one element parallel to the axis of the hooks 5 and 6, this axis itself being parallel to the edge of the blade resting in the hooks. According to the embodiment shown, two parallel guidance rods or elements 12 and 13 are attached by their ends to the small sides 7 and 8 of the frame and extend parallel to the sides 2 and 3. A probe support 14 slides along these elements 12 and 13 and is driven by the continuous probe displacement drive 15.

The probe support 14 consists of a carriage 16 having two bearings into which pass the rods 12 and 13. On its upper part the carriage has an elastic element 17 consisting of a plate spring, one of the ends of which is fixed onto the carriage and the other end of which supports a shoe 18 in which is housed the probe 19. The plate 17 is curved so that the shoe or at least that part of it housing the probe will rest, and can slide, on the under surface of the airfoil portion when the probe support is driven by the displacement drive 15. The drive consists of a linear movement transmission system which, in the embodiment shown, consists of a notched belt 20 mounted between two pinions 21 and 22 placed one at each end of the frame and parallel to the guidance elements. One of the pinions, for example pinion 21, is attached to the axis of a motor 30 positioned in or on the frame. A coupling part 23 provided on the carriage 16 cooperates with the notchings on the belt to drive the probe support 14.

In order to avoid damaging the shoe 18 and the probe 19 housed therein when the system is first placed on the airfoil portion of the blade, a shoe position is provided in which the spring 17 is forced against the carriage 16, thus releasing the shoe from the blade and making it possible to engage or disengage the edge of the blade with or from the hooks. This result is achieved by providing on the outside of the shoe 18 an inclined plane 24 (FIG. 2) that cooperates with a mating inclined plane 25 provided in the upper part of the hook 5. The starting position of the probe will therefore be the position in which the inclined planes matingly cooperate, during which the shoe will be held away from the blade.

Control elements including position detectors 100 and motor control 200 are provided at the end of the carriage's stroke in order to assure the stopping of the motor or reversal of the motor's direction.

Use (FIG. 3) of the system is as follows: with the aid of the handle 11, the system is introduced through the engine inspection hatches and into the area of the bladed wheel to be checked. The system is slid between two blades and the hooks 5 and 6 are placed on the blade leading edge 26 so that the probe is on the concave face of the blade. The system is then pivoted about the hooks so as to bring the inside of the stop 4 against the trailing edge of the blade. The motor 30 is then started which will cause the probe to go back and forth against the adjacent concave face of the leading edge. The system is withdrawn from the blade by a reverse operation and may be positioned on a neighboring blade.

The invention likewise extends to systems in which the elements described above are replaced by equivalent elements, and in particular to the utilization of guidance elements such as grooves, dovetails, or displacement means such as endless screws, or combined guidance and displacement drives such as a closed-circuit helically grooved shaft that performs the back-and-forth movement without reversing the motor's direction.

The system described and shown is provided for the exploration of a part of the concave face near the leading edge of the blade; it can be understood that by modifying the geometric position of the various parts the system can be adapted to any area of the blade and to any blade shape.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A system for the in situ checking of turbine engine blades by eddy currents, said system comprising:
 a frame including a first set of two parallel sides;
 positioning means on at least one of said sides for holding at least one of the edges of one of said blades;
 a detection probe;
 means connected to said frame and supporting said probe for rectilinear guidance of said probe parallel to said positioning means; and
 means connected to said frame for displacement of said probe along said means for rectilinear guidance,
 wherein said positioning means comprises:
 two C-shaped hook portions on one of said sides of said frame, a line extending between said hook portion being parallel to said one of said sides; and
 a stop attached to the other of said two sides,
 wherein the distance between said hook portions and said stop is substantially equal to the width of one of said blades.

2. The system of claim 1 wherein said means for displacement include a drive motor.

3. The system of claim 1 wherein said frame includes a second set of two parallel sides, and wherein said means for guidance further comprise two parallel elements, each having one end attached to one of said sides of said second set of parallel sides of said frame, said first portion of said means for rectilinear guidance being movable on said two parallel elements.

4. The system of claim 3 wherein said first portion of said means for rectilinear guidance comprises:
 a carriage movably cooperating with said two parallel elements;
 an elastic element having one end cooperating with said carriage; and
 a shoe holding said probe, said shoe being attached to the other end of said elastic element such that it is able to contact a blade mounted in said positioning means.

5. The system of claim 4 wherein said means for displacement comprises:
 a coupling element fixed to said first portion of said means for rectilinear guidance;
 a rectilinear movement transmission system connected between said frame and said coupling element; and
 a drive motor for said transmission system.

6. The system of claim 5 wherein said transmission system comprises:
 two pinions, one of said two pinions being mounted on each end of one of said sides of said first set of parallel sides;
 a notched belt mounted on said pinions and cooperating with said coupling element; and
 a two directional motor driving one of said pinions.

7. The system of claim 4 wherein said shoe includes an inclined plane portion and one of said hook portions includes a mating inclined plane portion, whereby said shoe is held by said one of said hook portions and away from said plane when said carriage is adjacent an end of said two parallel elements.

8. The system of claim 6 including:
 stopping means for the end positions of said carriage; and
 motor direction control means.

* * * * *